(12) United States Patent
Chen

(10) Patent No.: US 6,887,878 B2
(45) Date of Patent: May 3, 2005

(54) KMST ISOEUGENOL DERIVATIVES AND PHARMACEUTICAL ACTIVITY

(75) Inventor: Ing-Jun Chen, Kaohsiung (TW)

(73) Assignees: Ing-Jun Chen, Kaohsiung (TW); Syn-Rech Chem & Phan Co., Ltd, Hsin Ying (TW)

( * ) Notice: Subject to any disclaimer, the term of this patent is extended or adjusted under 35 U.S.C. 154(b) by 0 days.

(21) Appl. No.: 10/608,073

(22) Filed: Jun. 30, 2003

(65) Prior Publication Data

US 2004/0266785 A1 Dec. 30, 2004

(51) Int. Cl.$^7$ ..................... A61K 31/495; C07D 241/04

(52) U.S. Cl. .................................. 514/255.03; 544/394

(58) Field of Search ...................... 544/394; 514/255.03

(56) References Cited

FOREIGN PATENT DOCUMENTS

GB 966493 * 8/1964

OTHER PUBLICATIONS

Gupta et al. Arzneim.–Forsch./Drug Res. 28(1), p. 241–246 (1978).*
Dunn et al., Bibliographic record of "The reductions in sweetened milk intake induced by *interleukin–1 and endotoxin are not prevented by chronic antidepressant treatment*," http://www.hint.org.tw/cgi–bin/ovidweb/ovidweb.cgi., 2001.
Girard et al., "*A New Synthetic Flavonoid Protects Endothelium Derived Relaxing Factor–induced Relaxation in Rabbit Arteries in Vitro: Evidence for Superoxide Scavenging*," Biochemical Pharmacology, vol. 49, No. 10, pp. 1553–1539, 1995.
Altavilla et al., "*The Lazaroid, U–74389G, inhibits inducible nitric oxide synthase activity, reverses vascular failure and protects against endotoxin shock*,"European Journal of Pharmacology, vol. 369, pp. 49–55, 1999.
Aubriot et al., "*New Series of Aryloxpropanolamines with Both Human $\beta_3$–Adrenoceptor Agonistic Activity and Free Radical Scavenging Properties* ," Bioorganic & Medical Chemistry Letters, vol. 12, pp. 209–212, 2002.
Cohen et al., "*Evidence that Blood Pressure Reduction by Serotonin Antagonists is Related to Alpha Receptor Blockade in Spontaneously Hypertensive Rats*," Hypertension vol. 5, No. 5, pp. 676–681, Sep.–Oct., 1983.
Correa et al., "*Central $\alpha_1$–Adrenoceptors Mediate the Pressor Response to Intracerebroventricular Injection of Noradrenaline in Unanesthetized Rats*," Neuropharmacology vol. 34, No. 7, pp. 793–798, 1995.
Curro et al., "*Interaction Between Alpha Adrenergic and Serotonergic Activation of Canine Saphenous Veins*," The Journal of Pharmacology and Experimental Therapeutics vol. 207, pp. 936–949, 1978.

Diaz–Cabiale et al., "*Galanin/alpha2–receptor interactions in central cardiovascular control*," Neuropharmacology vol. 39, pp. 1377–1385, 2000.
Dobrucki et al., "*Central Hypotensive Action of Clonidine Requires Nitric Oxide*," Circulation, vol. 104, pp. 1884–1886, Oct. 16, 2001.
Duan et al., "*Enhancement of Clonidine–Induced Analgesia by Lesions Induced with Spinal and Intracerbroventricular Administration of 5, 7–Dihydroxytryptamine*," Neuropharmacology vol. 26, No. 4, pp. 323–329, 1987.
Duka et al., "*Role of the Postsynaptic $\alpha_2$–adrenergic receptor subtypes in catecholamine–induced vasoconstriction*," General Pharmacology vol. 34, pp. 101–106, 2000.
Elenkov et al., "*Modulation of lipopolysaccharide–induced tumor necrosis factor–$\alpha$production by selective $\alpha$–and $\beta$–adrenergic drugs in mice*," Journal of Neuroimmunology vol. 61, pp. 123–131, 1995.
Fujimoto et al., "*Denopamine as an $\alpha_1$H–adrenoceptor antagonist in isolated blood vessels*," European Journal of Pharmacology vol. 280, pp. 143–147, 1995.
Glaser et al., Bibliographic record of "*Stress depresses interferon production by leukocytes concomitant with a decrease in natural killer cell activity*, "http://www.int/org.tw/cgi–bin/ovidweb/ovidweb/cgi.

(Continued)

Primary Examiner—Richard L. Raymond
(74) Attorney, Agent, or Firm—Robert E. Bushnell, Esq.

(57) ABSTRACT

A compound having the following formula I:

$$R_1 \!-\!\!\bigcirc\!\!-\!X\!-\!N\!\!\bigcirc\!\!N\!-\!\!\bigcirc\!\!-\!R_2 \qquad (I)$$
$$\text{OMe}$$

where $R_1$ is an alkyl group or an alkenyl group, X represents $$-\text{OCH}_2\text{CHCH}_2-,$$
$$\;\;\;\;\;\;\;\;\;\;\;\;\;\;\;\;\;\;\;|$$
$$\;\;\;\;\;\;\;\;\;\;\;\;\;\;\;\;\;\;R_3$$

$R_2$ is selected from the group consisting of a halogen (o, m, p) group such as F, Cl, Br or I, —$NH_2$, —$NO_2$ and a hydrogen group, $R_3$ is a hydrogen group or OH. The compound has pharmacologically $\alpha_2$-adrenergic/5-$HT_{2A}$ antagonist activity, 5-HT re-uptake activity, and anti-oxidant activity. The compound is produced by preparing 4-epoxy isoeugenol, mixing piperazine dissolved in methanol with the 4-epoxy isoeugenol to reflux at 100° C. for approximately 2 to approximately 6 hours, removing the methanol, passing the mixture through a silica gel column chromatography after the removing step, eluting the passed mixture with n-hexane and ethyl acetate, drying the eluted mixture, and crystallizing the dried mixture with methanol.

10 Claims, No Drawings

OTHER PUBLICATIONS

Hasko et al., "Differential effect of selective block of $\alpha_2$–adrenoreceptors on plasma levels of tumour necrosis factor–$\alpha$, interleukin–6 and corticosterone induced by bacterial lipopolysaccharide in mice," Journal of Endocrinology vol. 144, pp. 457–462, 1995.

Hasko et al., "Differential effect of selective block of $\alpha_2$–adrenoreceptors on plasma levels of tumour necrosis factor–$\alpha$, interleukin–6 and corticosterone induced by bacterial lipopolysaccharide in mice," Journal of Endocrinology vol. 144, pp. 457–462, 1995.

Hatanaka et al., "Biochemical Profile of YM992, a Novel Selective Serotonin Reuptake Inhibitor with 5–$HT_{2A}$Receptor Antagonistic Activity," Neuropharmacology vol. 35, No. 11, pp. 1621–1626, 1996.

Helmeste et al., "Inhibitation of Platelet Serotonin Uptake by Cytochrome P450 Inhibitors Miconazole and Econazole," Life Sciences vol. 62, No. 24, pp. 2203–2208, 1998.

Hirata et al., "Effects of endothelin receptor antagonists on endothelin–1 and inducible nitric oxide synthase genes in a rat endotoxic model," Clinical Science, pp. 332–335, 2002.

Huang et al., "Inhibitory effect of DCDC on lipopolysaccharide–induced nitric oxide synthesis in RAW 264.7 cells," Life Sciences vol. 68, pp. 2435–2447, 2001.

Huang et al., "Ferulidiol : A Vasodilatory and Antioxidant Adrenoceptor and Calcium Entry Blocker, with Ancillary $\beta_2$–Agonist Activity," Drug Development Research 47:77–89 (1999).

Huang et al., "A New Aspect of View in Synthesizing New Type $\beta$–adrenoceptor Blockers with Ancillary Antioxidant Activities," Bioorganic & Medicinal Chemistry vol. 9, pp. 1739–1746, 2001.

Ko et al., "$\beta$–Blocker Therapy and Symptoms of Depression, Fatigue, and Sexual Dysfunction," JAMA vol. 288, No. 3, pp. 351–357, Jul. 17, 2002.

Koyama, "Participation of central $\alpha$–receptors on hemodynamic response to E. Coil endotoxin," American Journal Physiology vol. 247, pp. R655–R662, 1984.

Krege et al., "Affinity of trazodone for human penile$\alpha_1$—and $\alpha_2$–adrenoceptors," BJU International vol. 85, pp. 959–961, 2000.

Kubo et al., "Cardiovascular effects in rats of alpha$_1$and alpha$_2$adrenergic agen injected into the nucleus tractus solitarii," Naunyun–Schmiedeberg's Archives of Pharmacology vol. 335, pp. 274–277, 1987.

Lin et al., "Systemic Administration of Lipopolysaccharide Induces Release of Nitric Oxide and Glutamate and c–fos Expression in the Nucleus Tractus Solitarii of Rats," Hypertension 33:1218–1224, 1999.

Llado et al., "The $\alpha_2$–adrenoceptor antagonist idazoxan is an agonist at 5–$HT_{1A}$autoreceptors modulating serotonin synthesis in the rat brain in vivo", Neuroscience Letters vol. 218, pp. 111–114, 1996.

Loegering et al., "The Antioxidant, U74389, Ameliorates the Depression of Vascular Reactivity Caused by Lipopolysaccharide", Life Sciences, vol. 57, No. 20, pp. 321–326, 1995.

Maitra et al., "Alterations in Tissue Glucose Uptake During the Hyperglycemic and Hypoglycemic Phases of Sepsis", Hock vol. 13, No. 5, pp. 379–385, 2000.

Molina–Holgado et al., "Endotoxin Administration Induced Differential Neurochemical Activation of the Rat Brain Stem Nuclei," Brain Research Bulletin, vol. 40, No. 3, pp. 151–156, 1996.

Murphy et al., "Characterization of Alpha–2 Adrenergic Receptors in the OK Cell, an Opossum Kidney Cell Line," The Journal of Pharmacology and Experimental Therapeutics vol. 244, No. 2, pp. 571–578, 1987.

Nickola et al., "Antidepressant Drug–Induced Alterations in Neuron–Localized Tumor Necrosis Factor–$\alpha$mRNA and $\alpha_2$–Adrenergic Receptor Sensitivity," The Journal of Pharmacology and Experimental Therapeutics vol. 297, No. 2, pp. 680–687, 2001.

Owens et al., "Neurotransmitter Receptor and Transporter Binding Profile of Antidepressants and Their Metabolites," The Journal of Pharmacology and Experimental Therapeutics vol. 283, No. 3, pp. 1305–1322, 1997.

Pitzalis et al., "Depression but not anxiety influences the autonomic control of heart rate after myocardial infarction," American Heart Journal vol. 141, No. 5,pp. 765–771, 2001.

Shen et al., "Differential Effect of Chronic Antidepressant Treatments on Lipopolysaccharide–Induced Depressive––Like Behavioural Symptoms in the Rat," Life Sciences vol. 65, No. 17, pp. 1773–1786, 1999.

Smith et al., "Precontraction with Elevated Concentrations of Extracellular Potassium Enables both $5HT_{1B}$and 5–$HT_{2A}$"Silent" Receptors in Rabbit Ear Artery", The Journal of Pharmacology and Experimental Therapeutic vol. 289, No. 1, pp. 354–360, 1999.

Spengler et al., "Stimulation of $\alpha$–Adrenergic Receptor Augments the Production of Macrophage–Derived Tumor Necrosis Factor," The Journal of Immunology vol. 145, No. 5, pp. 1430–1434, Sep. 1999.

Sugita et al., "Inducible nitric oxide synthase plays a role in LPS–induced hyperglycemia and insulin resistance," Am J Physiol Endocrinol Metab vol. 282, pp. E–386–E394, 2002.

Szabo et al., Abstract of "Invited opinion : role of nitric oxide in hemorrhagic, traumatic, and anaphylactic shock and thermal injury," Shock. vol. 2, No. 2, pp. 145–155, Aug. 1994.

Szelenyi et al., "Differential involvement of sympathetic nervous system and immune system in the modulation of TNF–$\alpha$ production by $\alpha_2$–and $\beta$–adrenoceptors in mice," Journal of Neuroimmunology vol. 103, pp. 34–40, 2000.

Tseng et al., "Cardiovascular Effects of Nitric Oxide in the Brain Stem Nuclei of Rats," Hypertension vol. 27, pp. 36–42, 1996.

Tsuchiya et al., "Antioxidant Radical–Scavenging Activity of Carotenoids and Retinoids Compared to $\alpha$–Tocopherol," Methods in Enzymology vol. 213, pp. 460–472, 1992.

Ulker et al., "Endotoxin–Induced Vascular Hyporesponsiveness in Rat Aorta: In vitro Effect of Aminoguanidine," Pharmacological Research, vol. 44, No. 1, pp. 21–26, 2001.

Urban et al., "Involvement of $\alpha_2$–adrenoceptors in the cardiovascular effects of moxonidine," European Journal of Pharmacology, vol. 282 pp. 19–28, 1995.

Roux et al., "The effect of ketanserin on serotonin–induced vascular responses in the isolated perfused rat lung," European Journal of Pharmacology vol. 169, pp. 269–273, 1989.

Nueten et al., "Vascular Effects of Ketanserin(R 41 468), A Novel Antagonist of $5HT_2$Serotonergic Receptors," The Journal of Pharmacology and Experimental Therapeutics, vol. 218, No. 1, pp. 217–230, 1981.

Victor et al., "Ascorbic acid modulates in vitro the function of macrophages from mice with endoxtoxic shock," Immunopharmacology vol. 46, pp. 89–101, 2000.

Villalobos–Molina et al., "*The 5–HT$_2$ receptor antagonist, pelanserin, inhibits α$_1$–adrenoceptor–mediated vasoconstriction in vitro*," Journal of Pharmacology vol. 277, pp. 181–185, 1995.

Lang, "*Sepsis–induced insulin resistance in rats is mediated by a β–adrenergic mechanism*," Am J. Physiol vol. 263, pp. 703–711, 1992.

Lane et al., "*Selective Serotonin Reuptake Inhibitor–Induced Serotonin Syndrome: Review*," Journal of Clinical Psychopharmacology vol. 17, No. 3, pp. 208–221, Jun. 1997.

MacMillan et al., "*Central Hypotensive Effects of the α$_{2a}$–Adrenergic Receptor Subtype*," Science vol. 273, pp. 801–803, Aug. 1996.

Lavicky et al., "*Endotoxin Administration Stimulates Cerebral Catecholamine Release in Freely Moving Rats as Assessed by Microdialysis*," Journal of Neuroscience Research vol. 40, pp. 407–413, 1995.

Wu et al., "*Ascorbate inhibits iNOS expression in endotoxin– and IFNγ–stimulated rat skeletal muscle endothelial cells*," FEBS Letters vol. 520, pp. 122–126, 2002.

Wu et al., "*A Highly Selective β$_1$–Adrenergic Blocker with Partial β$_2$–Agonist Activity Derived from Ferulic Acid, an Active Component of Ligusticum wallichii Franch*," Journal of Cardiovascular Pharmacology vol. 31, pp. 750–757, 1998.

Wu et al., "*A xanthine–based KMUP–1 with cyclic GMP enhancing and K$^+$ channels opening activities in rat aortic smooth muscle*," British Journal of Pharmacology vol. 134, pp. 265–274, 2001.

Yeh, et al., "*Cardiovascular Interactions of Nonivamide, Glyceryl Nonivamide, Capsaicin Analogues, and Substance P Antagonist in Rats*," Brain Research Bulletin, vol. 30, pp. 641–648, 1993.

\* cited by examiner

KMST ISOEUGENOL DERIVATIVES AND PHARMACEUTICAL ACTIVITY

BACKGROUND OF THE INVENTION

1. Field of the Invention

Serotonergic and adrenergic receptors, functioning reciprocally in the central nervous and cardiovascular systems, are involved in the pharmacologic activities of some antidepressants. It is well established that noradrenaline neurons modulate the activity of the 5-HT(serotonin, 5-Hydroxytryptamine) system and several lines of evidence support the theory that the 5-HT system influences brain noradrenaline neurons (Villalobos-Molina R, et al., Eur. J. Pharmacol., 277:181–185,1995). Indeed, some selective or subtype-selective $\alpha_2$-adrenoceptor blockers, such as yohimbine, rauwolscine, and phentolamine, have been shown to possess an affinity for 5-HT$_{1A}$ receptors in the rat brain (Llado et al, 1996). Although $\alpha_2$-adrenoceptor blockers may provide some protection in rats against bacterial lipopolysaccharide (LPS)-induced hyperglycemia, tumor necrosis factor-$\alpha$ (TNF-$\alpha$), interleukin-6 (IL-6), corticosteroid release, and mortality (Haskó G. et al., J. Endocrinol., 144:457–462,1995; Hirata Y. and Ishimaru S., Clin. Sci., 103:332S–335S, 2002), similar protective functions provided by anti-depressants with $\alpha_2$-adrenoceptor and 5-HT blocking activities have not been investigated as thoroughly.

Lipopolysaccharide (LPS)-induced inflammatory cytokines, including tumor necrosis factor-$\alpha$ (TNF-$\alpha$), interleukin-1(IL-1) and interferon (IFN) could be regulated by blocking $\alpha_2$-adrenergic receptors, which are involved in the balance between noradrenergic and serotonergic systems in central neurons (Shen Y. et al., Life. Sci., 65:1773–1786, 1999). Despite the importance of LPS in inflammation, many aspects of LPS-induced dysfunction remain poorly understood. To date, the relationship between LPS-induced hypotension and high mortality is un-resolved. LPS is known to affect cerebral neurotransmission. The ability of $\alpha_2$-adrenoceptor blocking antidepressant treatment to attenuate LPS-induced-depression in rats has been cited as evidence that inflammatory cytokines play an important role in depression (Koyama, S. Am. J. Physiol., 16:R665–R662, 1984; Dunn A J. and Swiergiel A H., Neuroimmonomodulat., 9:163–169, 2001). It has been reported that selective blocking of $\alpha_2$-adrenoceptors located on noradrenergic axon terminals resulted in an increase in the release of noradrenaline (Haskó et al., 1995). In in vivo, $\alpha_2$- and $\beta$-adrenoceptors on macrophages can be activated by the endogenous ligand noradrenaline, released from noradrenergic varicosities and by adrenergic drugs. It is suggested that these increases regulate LPS-induced production of cytokines (Szelenyi J, Kiss J P and Vizi E S., J. Immunol., 103:34–40, 2000).

2. Description of the Related Art

2-Chlorphenyl-1-piperazinyl benzene (CPB) is a basic chemical structure, fuound in trazodone-like antidepressants with $\alpha_2$-adrenoceptor and 5-HT antagonist activities. Some $\beta$-adrenoceptor blockers, such as pindolol, have been found to have nanomolar binding affinities for 5-HT$_{1A}$ receptors and have prevented some 5-HT$_{1A}$ receptor-mediated responses (Haddjeri N, de Montigny C, and Blier P., Biol. Psychiat., 45:1163–1169, 1999). $\beta$-adrenergic blocking agents with serotonergic properties have proved beneficial to depressed patients, notably those with myocardial infarction and congestive heart failure (Pitzalis M V. et al., Am. Heart. J., 141:765–771, 2001); Valuck R J. et al., Dr. S., 10:511–516, 2001); Ko D T. et al., JAMA., 288:351–357, 2002). Aryloxypropanolamines, and especially those which are isoeugenol-based ones have been reported to have anti-oxidizing activities, in addition to their $\beta$-adrenoceptor blocking effects (Aubriot S. et al., Bioorgan. Med. Chem., 12:209–212, 1995; Huang Y C. et al., Drug. Dev. Res., 47:77–89, 1999; Bioorg. Med. Chem. 9:1739–1746, 2001). Trazodone, a well known antidepressant, with 5-HT agonist/antagonist activity, 5-HT reuptake inhibition and adrenoceptor blocking activities, was taken as a reference to evaluate associated pharmacologic activities (Cohen et al., 1983; Owens M J. et al., J. Pharmac. Exp. Ther., 283:1305–1322, 1997).

SUMMARY OF THE INVENTION

It is an object of the present invention to provide a compound having the formula I

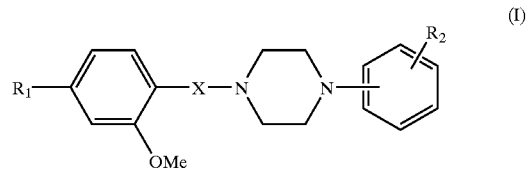

where $R_1$ is alkyl group or alkenyl group; X represents

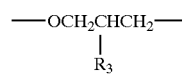

$R_2$ is selected from the group consisting of a halogen (o, m, p) group, —NH$_2$, —NO$_2$ and a hydrogen group; $R_3$ is a hydrogen group or OH; and n is 0 to 2. The halogen group is preferably F, Cl, Br or I. It is also an object to provide the isoeugenol derivative having pharmacologically $\alpha_2$-adrenergic/5-HT$_{2A}$ antagonist, 5-HT re-uptake inhibition, and anti-oxidant activities. It is further an object to provide a method of the compound.

DETAILED DESCRIPTION OF THE INVENTION

The invention disclosed some isoeugenol derivatives pharmacologically with $\alpha_2$-adrenergic/5-HT$_{2A}$ antagonist, 5-HT re-uptake inhibition, anti-oxidant activities, anti-platelet aggregation and anti-septic shock activities.

The compound is shown as formula I,

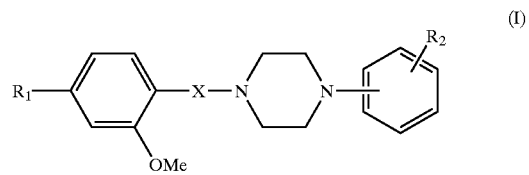

Where $R_1$ is alkyl group or alkenyl group;
X represents

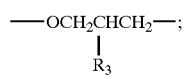

$R_2$ is a halogen (o, m, p), —NH$_2$, —NO$_2$ or a hydrogen group, wherein the halogen is F, Cl, Br or I.
$R_3$ present a hydrogen group or OH; and n is 0 to 2.
Epichlorohydrin was mixed with isoeugenol and NaOH dissolved in ethanol, boiled to reflux for 2–6 hours. The included ethanol was removed from the mixture, and the mixture is passed through silica gel column chromatography, eluated with n-hexane and ethyl acetate, dried with reduced pressure and obtained 4-oxy-methyloxirane-3-methoxy-1-propylenyl benzene. Piperazine was dissolved in methanol, mixed with 4-oxy-methyloxirane-3-methoxy-1-propylenyl benzene to reflux at 100° C. for 2–6 hours. Obtained mixture was then removed the included methanol by reduced pressure using vacuum pump. The residue was passed through silica gel column chromatography, eluated with n-hexane and ethyl acetate, dried by reduced pressure, and crystallized with methanol to obtain white crystal of compound.

With the view of developing an anti-depressant with enhanced anti-oxidizing, $\alpha_2$-adrenoceptor blocking, cytokine inhibiting, and pindolol-like-$\beta$-adrenoceptor blocking activities, we first synthesized KMST by combining isoeugenol-based oxypropanolamine and CPB(2-chlorphenyl-1-piperazinyl benzene).

We hypothesized that this produced KMST, which chemically has an anti-oxidant oxypropanolamine base, may reveal CPB-related $\alpha_2$-adrenoceptor and 5-HT receptor antagonist properties, including inhibition of LPS-induced hypotension, hyperglycemia, and cytokine formation. In the present study, we examined the receptor binding affinity and blockade of 5-HT re-uptake, 5-HT and adrenergic receptor inhibition, anti-oxidant, peroxyl radical scavenging, and cardiovascular responses regulated by KMST in the CNS (central neuron systems). Particularly, we emphasized the inhibitory activities of KMST, compared with those of anti-depressant trazodone, on LPS-induced hypotension, hyperglycemia, and cytokine formation.

Pharmacological Activities

This invention compound has been proven by the following pharmacological experiments that follow.

Animals

Wistar rats were provided from National Laboratory Animal Breeding and Research Center (Taipei, Taiwan). They were housed under conditions of constant temperature and controlled illumination (light on between 7:30 and 19:30). Food and water were available ad libitum. The study was approved by the Animal Care and Use Committee of Kaohsiung Medical University.

Drugs and Chemicals

Yohimbine, 5-nonyloxytryptamine, methylsergide, clonidine, isoprenaline, ketanserin, noradrenaline, serotonin, and aminoguanidine HCl were purchased from Sigma Chemical Co. (St. Louis, Mo., U.S.A.). Trazodone was obtained from Lotus Medical Supply (Taipei). KMST synthesized in this laboratory was solvated in 50% absolute alcohol, 10% propylene glycol and further dilutions of distilled water. All of the [$^3$H]ligand was purchased from New England Nuclear Corp. (Boston, Mass., U.S.A.). Nonspecific-ligand (10 $\mu$M): serotonin, phentolamine, propanolol and specific [$^3$H]-ligand (nM): WAY100635 (1), GR125743 (3), ketanserin (0.5), prazosin (0.2), yohimbine (2), CGP12177 (1 and 3) were used in the displacement experiment for different types of receptors.

Intravenous Injection

The experiments were carried out as previously described (Wu B N. et al., *Biochem. Pharmacol.*, 48:101–109, 1994). In brief, Wistar rats weighing 250–300 g were anesthetized with pentobarbital sodium (50 mg kg$^{-1}$, i.p.). Following tracheal cannulation, systemic arterial BP and HR were recorded from the femoral artery by a pressure transducer (model P10EZ; Spectramed, Oxnard, Calif., U.S.A.) connected to a recorder (GOULD, Valley View, Ohio, Model P50). Body temperature was maintained at 37° C. by an electric heating pad. A femoral vein was cannulated for intravenous injection of drugs and LPS (10 mg kg$^{-1}$). Pretreatment with KMST, yohimbine or trazodone (0.5, 1 mg kg$^{-1}$, i.v.) and aminoguanidine or ascorbic acid (15 mg kg$^{-1}$, i.v.) 15 minutes before LPS injection was followed by recording BP changes 1, 3, and 5 hours after LPS injection.

Adrenergic Receptor Antagonist Activities

KMST ($10^{-8}$, $10^{-7}$, $10^{-6}$ M) competitively inhibited cumulative noradrenaline- and clonidine-induced contractile activities. The pA$_2$ value of KMST for $\alpha_1$ and $\alpha_2$-adrenergic receptors were 7.97±0.39 and 7.40±0.38, respectively (Table 1). Regarding $\beta_1$-adrenoceptor blocking activity in electrically stimulated left atria, KMST ($10^{-8}$, $10^{-7}$, $10^{-6}$ M) concentration-dependently inhibited cumulative isoprenaline-induced positive inotropic effects. The apparent pA$_2$ value of regression lines for KMST was 6.66±0.17 (Table 1).

5-HT$_{2A}$ Receptor Antagonist Activity

KMST ($10^{-8}$, $10^{-7}$, $10^{-6}$ M) concentration-dependently inhibited cumulatively added 5-HT-induced contractile activities in isolated rat thoracic aortas. Table 1 shows the pA$_2$ value (8.68±0.12) and slope of regression lines for KMST and other agents on 5-HT$_{2A}$ receptor. Other $\beta$-adrenoceptor blockers had no influence on the contractile response to 5-HT.

Receptor Binding Activity

In this study, KMST, propranolol, prazosin, ketanserin, methylsergide and 5-HT all produced competitive binding activity with [$^3$H]GR125743 (5-HT$_{1B/1D}$)and, [$^3$H]ketanserin (5-HT$_{2A}$) on serotonergic receptors in rat cortex, with [$^3$H]prazosin on $\alpha_1$ receptors in rat cortex, with [$^3$H]yohimbine on $\alpha_2$ receptors in rat cortex, with [$^3$H]CGP-12177 on $\beta_1$ receptors in rat ventricl and with [$^3$H]CGP-12177 on $\beta_2$ receptors in rat lung. KMST had a higher binding affinity than other $\beta$-adrenergic antagonists for 5-HT$_{2A}$ receptors. The order of potency on 5-HT$_2$A receptors was ketanserin>methylsergide>KMST>5-HT>propranolol>prazosin. Methylsergide and 5-HT had lower binding affinities for $\alpha_1$ receptors. The order of $\alpha_1$ receptor binding potency was prazosin>ketanserin>KMST>methylsergide, propranolol and 5-HT. Prazosin had strong $\alpha_1$- and $\alpha_2$-adrenoceptor affinities. Ketanserin, methylsergide and KMST also had binding affinities for $\alpha_2$-adrenoceptors. The order of $\alpha_2$ receptor binding potency was prazosin>KMST>ketanserin>methylsergide>propranolol and 5-HT. Propranolol had high $\beta_1\beta_2$-adrenoceptor-affinity. In striking contrast, KMST had lower binding affinity for $\beta_2$-adrenoceptors. The Ki values of KMST and other reference compounds are indicated in Table 2.

Inhibitory Activities of 5-HT Re-Uptake

The IC50 values of 5-HT uptake inhibition by KMST and trazodone in rat cortex were 3.426×10$^{-5}$ M and 1.164×10$^{-6}$ M, respectively. Although KMST was not as potent as trazodone, it potently inhibited 5-HT cortical uptake.

Anti-Oxidant and Peroxyl Radical Scavenging Activities

In order to eliminate the possibility that KMST and other test compounds interfered with the assay, the test agents were added directly to MDA (malondialdehyde) standard before the TBA reagent was added. The abilities of KMST and other test compounds to inhibit lipid peroxidation in rat brain homogenate were compared (Table 3). KMST dose-dependently inhibited Fe$^{2+}$-ascorbic acid-induced lipid peroxidation in rat brain homogenate with an IC$_{50}$ of 2.681±0.05 $\mu$M (n=5). The potency of KMST was approximately 5, 30 and 3 times that of yohimbine, trazodone and ascorbic acid, respectively (Table 3).

Protective Effects on LPS-Induced Vascular Hyporeactivity

The isolated aortas from LPS-treated rats were hyporeactive to phenylephrine ($10^{-8} \sim 10^{-4}$ M) in vitro. Intravenous injection of KMST (1 mg kg$^{-1}$) before or after application of LPS improved the aortic contractility better than in vehicle group. One hour after administration of LPS, vascular contractility was similar to that of controls. In comparison with yohimbine, trazodone, aminoguanidine and ascorbic acid, KMST was more effective in protecting from LPS-induced hyporeactivity of the aorta. For all agents administered 1 hour after LPS injection, the resulting hyporeactivity in aorta and estimated $pD_2$ values of all agents were similar to each other; but $pD_2$ value of yohimbine and trazodone at 5 hour was less than KMST, ascorbic acid, and aminoguanidine (Table 4). $pD_2$ indicates the value of $-\log EC_{50}$, $EC_{50}$ said the dose produced the effect in 50% of the animals.

Platelet Aggregation.

Venous blood from human volunteer donors was collected in 10 ml Monovette containing 1 ml citrate solution (0.106M trisodium citrate; Sarstedt, Numbrecht, Germany) and centrifuged (400 g, 10 min, 20° C.). The platelet-rich plasma (PRP) was removed and mixed with one-fourth volume of ACD buffer (44.8 mM sodium citrate, 20.9 mM citric acid, 74.1 mM glucose, pH 5.0). After centrifugation (10 min, 2000 g, 20° C.), the platelet pellet was resuspended in wishing buffer (113 mM NaCl, 4 mM $Na_2HPO_4$, 24 mM $NaH_2PO_4$, 4 mM KCl, 0.2 mM EGTA(Ethylene glycol-bis-(2-aminoethyl ether) N,N,N'-tetraacetic acid), 0.1% (wt/vol) glucose, pH 6.0) and recentrifuged (10 min, 2000 g, 20° C.). The washed platelets were resuspended in incubation buffer (134 mM NaCl, 12 mM $NaHCO_3$, 2.9 mM KCl, 0.34 mM $NaH_2PO_4$, 5 mM HEPES (N-(2-hydroxyethyl) piperazine-N'-(2-ethanesulfonic acid)), 5 mM glucose, pH7.4), cells were counted in a Sysmex hematology analyzer (Sysmex, CDA-500, Japan) and adjusted to a final concentration of $2 \times 10^8$ platelets/ml.

The aggregation of the platelets in platelet-rich plasma (PRP) was measured as a change in light absorbance by a Payton dual-channel aggregometer (NBS, Hema tracer, Japan). PRP (240 µL) was stirred (700 rpm) at 37° C. for 1 min, and 5 µL epinephrine (final concentration 5 µM), serotonin (final concentration 5 µM) was added. After which the rate of primary aggregation (1/min) and maximum aggregation (%) at 5 min were recorded. To study the effects of compounds on epinephrine or serotonin-induced aggregation, PRP was incubated with 5 µL of compounds at various concentrations for 1 min before epinephrine or serotonin was added. $IC_{50}$ values given were calculated from the secondary aggregation data.

DETAILED DESCRIPTION OF EXPERIMENTS

Intra-Cisternal Injections

Intra-cisternal injections of KMST (0.3, 0.03 µmol), yohimbine [0.03 µmol), and clonidine (38 pmol), were performed in rats as described by Duan et al (1987). Briefly, rats weighing 250–300 g were anaesthetized with pentobarbital sodium (50 mg kg$^{-1}$, i.p.) and mounted in a David-Kopf stereotaxic instrument (Yeh J L. et al., Brain. Res. Bull., 30:641–648, 1993). The calvarium was exposed and a 1 mm diameter trephine hole was drilled 1.8 mm lateral to the coronary and 1.5 mm posterior to the sagittal sutures. A cannula (0.7 mm O.D.) connected to a Hamilton syringe (RN-705, 5051) by PE-50 was advanced 4.7 mm into the brain using the electrode carrier.

Micro-Injection in NTS

Rats were anesthetized and placed in a David-Kopf stereotaxic instrument. The cerebellum was exposed after removing the skin and occipital bone. The NTS coordinates were (reference to lambda) P 5–6 mm, L/R 0.5–1 mm, depth 6–7.5 mm (Wu et al., 1994). NTS injection sites were confirmed by decreasing BP and HR following microinjection of 1% L-glutamate. KMST (0.3, 0.03 µmol), trazodone (0.3, 0.03 µmol) and yohimbine (0.03 µmol) were then injected. Pre-treatment with clonidine was performed 15 min before administration of test agents. At the end of experiments, the animals were sacrificed. The brain was removed and sectioned for histological confirmation of the drug application site.

Isolation of Rat Thoracic Aorta

Rat thoracic aorta was removed, cleaned of adhering fat and connective tissue and cut into 3–4 mm wide transverse rings, which were then mounted at 1 g resting tension on stainless steel hooks in a 10 ml organ bath, bathed at 37° C. in physiological solution (mM: NaCl 118, KCl 4.8, $CaCl_2$ 2.5, $MgSO_4$ 1.2, $KH_2PO_4$ 1.2, $NaHCO_3$ 24, glucose 11), and aerated with a 95% $O_2$ and 5% $CO_2$ mixture. Isometric tension of aortic rings was monitored by a force displacement transducer (UGO BASILE, Model 7004, Italy). Tissue was equilibrated for 1 hr in physiological solution (Wu B N. et al., Br. J. Pharmacol., 134:265–274, 2001). Clonidine, noradrenaline and serotonin ($10^{-8} \sim 10^{-4}$ M) were added to the bath to induce contractions after pretreatment with KMST for 15 min.

Isolation of Rat Left Atria

Rats of either sex weighing 350–500 g were sacrificed after mild anesthesia with ether, and their hearts were quickly excised. Left atria were dissected from the hearts and mounted in a 10 ml organ bath with one end fixed and the other end connected to a force displacement transducer (Grass, Model FT03). The experiments were carried out at 37° C. in a Krebs solution of the following composition (mM): NaCl 113, KCl 4.8, $CaCl_2$ 2.2, $KH_2PO_4$ 1.2, $MgCl_2$ 1.2, $NaHCO_3$ 25, Dextrose 11.0; bubbled with a 95% $O_2$+5% $CO_2$ mixture. Atria were pre-stretched to a baseline tension of 0.5 g and equilibrated for 60 min in an aerated Krebs solution before starting experimental protocols. Atria were driven at 2-s intervals via two platinum electrodes on each side. An incubation time of 30 min was allowed for the test compound. Data were calculated as a percentage of the maximum contraction (Wu et al., 2001).

Receptor Binding Studies

Wistar rat cortex (for $\alpha_1$, $\alpha_2$-adrenoceptor, serotonergic receptor binding), heart (for $\beta_1$-adrenoceptor binding), and lung (for $\beta_2$-adrenoceptor binding) were homogenized with a Kinematica polytron in 20 volumes of ice-cold TE buffer (10 mM Tris HCl, 1 mM EDTA(ethylenediaminetetraacetic acid), 0.1 mM ascorbic acid, pH 7.4) (Wu et al., 1994). The homogenate was pressure filtered through muslin. Filtrate was centrifuged at 1000 g for 10 min. Supernatant was centrifuged at 10,000 g for 12 min at 4° C. The second supernatant was centrifuged at 30,000 g for 15 min at 4° C. The final pellet was re-suspended in assay buffer (75 mM Tris HCl, 25 mM $MgCl_2$, pH 7.4). Protein content was determined by Bradford's method. Radioligand agents and membranes (200–300 µg) were incubated for 60 min at 25° C. with or without the addition of nonspecific binding agents, in a 75 mM Tris HCl buffer with 25 mM $MgCl_2$, to make a final volume of 500 µl. In competitive-binding experiments, the competing agent was added directly to the incubation mixture. Incubation was terminated by addition of 1 ml of ice-cold assay buffer followed by immediate filtration through Whatman GF/C glass fiber filters supported on a 12-port filter manifold (Millipore). The filters were immediately washed 3 times with 5 ml of ice-cold assay buffer and dried in an oven at 60° C. for 2 hours before adding 5 ml of Triton-toluene-based scintillation fluid. Membrane-bound radioligand trapped in the filters was counted in a Beckman LS6500 scintillation system (Fullerton, Calif., U.S.A) with an efficiency of 45%. In each experiment, nonspecifically bound radioligand agents were determined by incubating membrane protein. Specific binding for each sample was obtained by deducting this value from the total binding of radioligand agents.

5-HT Re-Uptake Studies in Cerebral Cortex

Inhibition of 5-HT reuptake was measured by slight modification of the method of Hatanaka K. et al. (Neuropharmacology., 35:1621–1626, 1996) and Helmeste et al. (Life. Sci., 62:2203–2208, 1998). Wistar rats weighting 150–200 g were decapitated, the cerebral cortex or striatum was dissected and crude synaptosomes were prepared. The crude synaptosomes were suspended in about 16 mg wet tissue per 1 ml of Krebs buffer for 5-HT uptake. Uptake was initiated by the addition of 50 $\mu$l of [$^3$H] 5-HT to give a final concentration (30 nM), continued for 2 min at 37° C., and terminated by cooling the mixture in an ice bath. Saline was added to the incubation mixture, which was then filtered through a Whatman GF/B glass filter under reduced pressure. To determine nonspecific uptake, incubation was performed at 0° C.

Anti-Oxidant and Peroxyl Radical Scavenging Activities

Rat brain homogenate was made in 0.9% saline containing 10 mg tissue/ml. The rates of membrane lipid peroxidation were measured by the formation of thiobarbituric acid (TBA)-reactive substance (TBARS). Rat brain homogenates (1 ml) were incubated at 37° C. for 5 min with 10 $\mu$l of test compound or vehicle. Lipid peroxidation was initiated by the addition of 0.1 ml of 0.25 mM $FeCl_2$ and 1 mM ascorbic acid (Huang Y C. et al., Drug. Dev. Res., 47:77–89, 1999). After 30 min of incubation, the reaction was stopped by adding 0.1 ml of 0.2% BHT. TBA reagent was then added and the mixture was heated for 30 min in a boiling water bath. TBARS was extracted by n-butanol and measured at 532 nm. The amount of TBARS was quantified using the linear regression obtained from malondialdehyde (MDA) standards.

The scavenging ability of the test compounds on aqueous peroxyl radicals was determined by the method described by Tsuchiya M. et al. (Methods Enzymol., 213:460–472, 1992). The stoichiometric factors of the test compounds with hydrophilic peroxyl radicals were calculated by the equation as mentioned Ascorbic acid was used as a positive control.

Plasma Cytokine Immunoreactivity and Blood Glucose

Blood was collected from venous cannula, injected into ice-cold heparinized Eppendorf tubes and centrifuged at 1500 rpm for 10 min at 4° C. Plasma supernatant was stored at −70° C. until analyzed. Solid phase enzyme immunoassay that specifically detects murine IL-1$\beta$, IL-6, IFN-$\gamma$ and TNF-$\alpha$ was used with a detection limit of >10 pg/ml (Endogen, U.S.A). Pre-treatment with KMST and other agents was performed 15 minutes before intravenous injection of LPS. Blood was collected from venous cannula. Blood glucose was measured with a glucose test strip (Glucotide, Bayer, U.S.A) at 1, 3 and 5 hours.

Statistical Evaluation of Data

Results are expressed as mean±SD (statistical differences). Statistical differences were determined by independent and paired Student's t-test in unpaired and paired samples. Whenever a control group was compared with more than one treated group, the one-way ANOVA (analysis of variance) or two-way repeated measures ANOVA was used. When the ANOVA manifested a statistical difference, Dunnett's or Student-Newman-Keuls test was applied. $P<0.05$ was considered to be significant. Analysis of data were done with the aid of software (SigmaStat and SigmaPlot, Version 5.0, San Rafael, Calif., U.S.A.; GraphPad PRISM™, Version 2.0, San Diego, Calif., U.S.A.) run on an IBM-compatible computer and a Power Macintosh.

Results

Adrenergic Receptor Antagonist Activities

KMST ($10^{-8}$, $10^{-7}$, $10^{-6}$ M) competitively inhibited cumulative noradrenaline- and clonidine-induced contractile activities. The $pA_2$ values of KMST for $\alpha_1$- and $\alpha_2$-adrenergic receptors were 7.97±0.39 and 7.40±0.38, respectively (Table 1).

TABLE 1

$pA_2$ values for KMST and other reference compounds in isolated aorta and atria of Wistar rats

| Agents | 5-HT$_{2A}$ pA$_2$ value | $\alpha_1$ pA$_2$ value | $\alpha_2$ pA$_2$ value | $\beta_1$ pA$_2$ value |
| --- | --- | --- | --- | --- |
| KMST | 8.68 ± 0.12 | 7.97 ± 0.39 | 7.40 ± 0.38 | 6.66 ± 0.17 |
| Propranolol | NS | NS | NS | 8.32 ± 0.09 |
| Prazosin | NS | 9.73 ± 0.03 | 10.23 ± 0.10 | NS |
| Ketanserin | 9.08 ± 0.08 | 7.74 ± 0.32 | NS | NT |

The $pA_2$ values, evaluated at aorta for 5-HT$_{2A}$, $\alpha_1$, $\alpha_2$, at atria for $\beta_1$, were calculated from individual Schild plot by regression analysis. Each $pA_2$ value was the mean ± SEM of eight experimental results.
NS: not significant.
NT: not tested.

Regarding $\beta_1$-adrenoceptor blocking activity in electrically stimulated left atria, KMST ($10^{-8}$, $10^{-7}$, $10^{-6}$ M) concentration-dependently inhibited cumulative isoprenaline-induced positive inotropic effects. The apparent $pA_2$ value of regression lines for KMST was 6.66±0.17 (Table 1).

5-HT$_{2A}$ Receptor Antagonist Activity

KMST ($10^{-8}$, $10^{-7}$, $10^{-6}$ M) concentration-dependently inhibited cumulatively added 5-HT-induced contractile activities in isolated rat thoracic aorta. Table 1 shows the $pA_2$ value (8.68±0.12) and slope of regression lines for KMST and ketanserin on 5-HT$_{2A}$ receptors. Propranolol had no influence on the contractile response to 5-HT.

Receptor Binding Activity

In this study, KMST, propranolol, prazosin, ketanserin, methysergide and 5-HT all produced competitive binding activities on $\alpha_1$-adrenoceptors, $\alpha_2$-adrenoceptors and serotonergic receptors in rat cortex, respectively, against the following ligands: [$^3$H]prazosin ($\alpha_1$), [$^3$H]yohimbine ($\alpha_2$), [$^3$H]GR125743 (5-HT$_{1B/1D}$), [$^3$H]ketanserin (5-HT$_{2A}$). [$^3$H] CGP-12177 was used in the measurements of competitive binding activities on $\beta_1$ receptors in rat ventricle and on $\beta_2$ receptors in rat lung. The Ki values (nM) of KMST and other reference compounds are indicated in Table 2. KMST (Ki= 33.29) had a higher binding affinity than propranolol for 5-HT$_{2A}$ receptors. Methysergide and 5-HT had lower binding affinities for $\alpha_1$ receptors. Prazosin had strong $\alpha_1$- and $\alpha_2$-adrenoceptor affinities. In contrast, KMST's $\alpha_1$-adrenoceptor(Ki=141.94) affinities were lower than prazosin. Ketanserin, methysergide and KMST (Ki=1386.14) also had binding affinities for $\alpha_2$-adrenoceptors. Propranolol had high $\beta_1$- and $\beta_2$-adrenoceptor affinities. In striking contrast, KMST (Ki>10000) had a lower binding affinity for $\beta_2$-adrenoceptors.

TABLE 2

Affinity Constants for KMST and Other Reference Compounds in Wistar rat and guinea pig

| Agents | 5-$HT_{1A}$ | 5-$HT_{1B}$ | 5-$HT_{2A}$ | $\alpha_1$ | $\alpha_2$ | $\beta_1$ | $\beta_2$ | $M_2$ |
|---|---|---|---|---|---|---|---|---|
| 1 | >10000 | 669.9 | 33.29 | 141.94 | 1836.14 | 72.77 | >10000 | >10000 |
| 2 | >10000 | 1093.02 | 2.99 | 46.99 | 1965.31 | 106.25 | >10000 | >10000 |
| 3 | >10000 | 770.35 | 3.11 | 141.56 | 9285.61 | 113.42 | >10000 | >10000 |
| Isoeugenolol | — | — | 585.12 | >10000 | >10000 | 209 | 6859 | — |
| Isoeugenodilol | — | — | 1007.14 | 38.91 | 9699.43 | 43.61 | 53.71 | — |
| Atenolol | — | — | >10000 | >10000 | >10000 | 262.76 | 8511.4 | — |
| Labetalol | — | — | 612.13 | 52.48 | 3542.91 | 4.17 | 52.48 | — |
| Propranolol | — | — | 202.04 | >10000 | >10000 | 0.23 | 0.55 | — |
| Prazosin | — | — | 2489.81 | 1.53 | 163.93 | — | — | — |
| Ketanserin | >10000 | >10000 | 0.047 | 15.81 | 2274.99 | — | — | — |
| Methsergide | >10000 | >10000 | 4.411 | >10000 | 2427.03 | — | — | — |
| 5-HT | 0.013 | 70.33 | 152.91 | >10000 | >10000 | — | — | — |
| 5-nonyloxytryptamine | — | 5.81 | — | — | — | — | — | — |

Ki values were calculated from the equation Ki=$IC_{50}$/(1+ [$^3$H]ligand/Kd).
Kd and [$^3$H]ligand denote the apparent dissociation contrast and the free concentration of the radiolabel, respectively.

Inhibitory Activities of 5-HT Re-Uptake

The $IC_{50}$ values of 5-HT uptake inhibition by KMST and trazodone in rat cortex were $3.426 \times 10^{-5}$ M and $1.164 \times 10^{-6}$ M, respectively. Although KMST was not as potent as trazodone, it strongly inhibited 5-HT cortical uptake.

Anti-Oxidant and Peroxyl Radical Scavenging Activities

In order to eliminate the possibility that KMST and other test compounds interfered with the assay, the test agents were added directly to MDA standard before the TBA reagent was added. The abilities of KMST and other test compounds to inhibit lipid peroxidation in rat brain homogenate were compared (Table 3). KMST dose-dependently inhibited $Fe^{2+}$-ascorbic acid-induced lipid peroxidation in rat brain homogenate with an $IC_{50}$ of $2.681 \pm 0.05$ $\mu$M (n=5). The potency of KMST was approximately 5, 30 and 3 times that of yohimbine, trazodone and ascorbic acid, respectively (Table 3).

TABLE 3

Fifty inhibition concentration ($IC_{50}$) required in inhibiting lipid peroxidation initiated by $Fe^{2+}$-ascorbic acid in rat brain homogenates

| Compounds | $IC_{50}(\mu M)$ |
|---|---|
| KMST | 2.68 ± 0.27 |
| Yohimbine | 11.09 ± 0.35 |
| Trazodone | 60.61 ± 0.76 |
| Aminoguanidine | >100 |
| Ascorbic acid | 7.15 ± 0.14 |

Protective Effects on LPS-Induced Vascular Hyporeactivity

Isolated aortas from LPS-treated rats were hyporeactive to phenylephrine ($10^{-8} \sim 10^{-4}$ M). Intravenous injection of KMST (1 mg $kg^{-1}$) before or after application of LPS increased aortic contractility more than the vehicle group. One hour after administration of LPS, vascular contractility was similar to that of controls. In comparison with yohimbine, trazodone, aminoguanidine and ascorbic acid, KMST was more effective in protecting from LPS-induced hyporeactivity of the aorta. When all agents were administered 1 hour after LPS injection, aortic hyporeactivity and estimated $pD_2$ values of all agents were similar; however, $pD_2$ values of yohimbine and trazodone at 5 hours were less than those of KMST, ascorbic acid and aminoguanidine (Table 4).

TABLE 4

The $pD_2$ values to phenylephrine-induced contractions in rat thoracic aorta

| | $pD_2$ at 3rd hr | $pD_2$ at 5th hr |
|---|---|---|
| Control | 7.29 ± 0.15 | 7.35 ± 0.24 |
| LPS | 5.72 ± 0.27 | 4.94 ± 0.13 |
| Before LPS injection (30 min) | | |
| Vehicle | 5.84 ± 0.21 | 4.91 ± 0.18 |
| KMST | 7.16 ± 0.18* | 6.29 ± 0.11* |
| Yohimbine | 6.73 ± 0.33* | 3.44 ± 0.22 |
| Trazodone | 6.29 ± 0.21* | 3.99 ± 0.16 |
| Aminoguanidine | 6.81 ± 0.17* | 5.44 ± 0.31* |
| Ascorbic acid 1 mg kg-1 | 7.07 ± 0.25* | 5.04 ± 0.28 |
| Ascorbic acid 15 mg kg-1 | 6.71 ± 0.13* | 5.11 ± 0.22 |
| Control | 7.32 ± 0.22 | 7.31 ± 0.19 |
| LPS | 5.85 ± 0.39 | 4.99 ± 0.16 |
| After LPS injection (1 hr) | | |
| Vehicle | 5.75 ± 0.21 | 4.98 ± 0.19 |
| KMST | 6.29 ± 0.08* | 5.57 ± 0.17* |
| Yohimbine | 6.12 ± 0.14 | 5.13 ± 0.26 |
| Trazodone | 6.01 ± 0.09 | 5.04 ± 0.11 |
| Aminoguanidine | 6.48 ± 0.13* | 5.81 ± 0.14* |
| Ascorbic acid 15 mg kg-1 | 6.64 ± 0.16* | 5.21 ± 0.12* |

The statistical analysis was performed using Student-Newman-Keuls test.
*Significantly different from control, p < 0.05.
The $pD_2$ value of agent of each group was compared with the values of LPS of each group.

Inhibition of LPS-Induced Cytokine Immunoreactivities and Hyperglycemia 1, 3 and 5 hours after LPS 10 mg $kg^{-1}$, i.v.) administration, immunoreactivities of IL-1β, IL-6, IFN-γ and TNF-α were increased. After pretreatment with LPS, none of the administered agents significantly reduced LPS-induced increases in various cytokines. Yohimbine and ascorbic acid insignificantly enhanced LPS-induced production of IFN-γ at 1 hour after LPS administration.

Anti-Platelet Aggregation

The inhibitory activities of compounds 1–3 on serotonin- or epinephrine-induced platelet aggregations were shown on Table 5. The $IC_{50}$ of compounds 1, 2 and 3 in serotonin-induced experiments were $3.63 \times 10^{-9}$ M, $4.73 \times 10^{-9}$ M and $5.3 \times 10^{-7}$ M, respectively, and $2.78 \times 10^{-6}$ M, $3.9 \times 10^{-6}$ M and $4.38\times10^{-9}$ M in epinephrine-induced ones (Table 5). The $IC_{50}$ value was 10 nM for ketanserin; compounds 1, 2 and 3 were $3.63\times10^{-9}$, $4.73\times10^{-9}$ and $5.3\times10^{-7}$ M, respectively. It is obvious that compounds 1 and 2 were more effective than ketanserin to inhibit serotonin-induced platelet aggregations. The estimated $IC_{50}$ value for yohimbine to inhibit epinephrine-induced platelet aggregation was $9.8\times10^{-7}$ M (Mustonen et al., 2000). In our data, the estimated $IC_{50}$ values of compound 1, 2 and 3 to antagonize epinephrine-induced platelet aggregation were $2.78\times10^{-6}$, $3.9\times10^{-6}$ and $4.38\times10^{-9}$ M, respectively. Compound 3 was more potent than yohimbine in epinephrine-induced platelet aggregation. Alpha-adrenergic receptors of human platelets are exclusively of $\alpha_2$-subtype (Bylund et al., 1988). Our results indicated that compounds 1–3 were belong to non-selective inhibitors of $5-HT_{2A}$ and $\alpha_{2A}$ receptors in platelet aggregations (Table 2).

TABLE 5

IC50 (M) of compounds 1–3 on serotonin or epinephrine-induced human platelet aggregation

| Compounds | Serotonin | Epinephrine |
| --- | --- | --- |
| 1 | $3.63 \times 10^{-9}$ | $2.78 \times 10^{-6}$ |
| 2 | $4.73 \times 10^{-9}$ | $3.9 \times 10^{-6}$ |
| 3 | $5.3 \times 10^{-7}$ | $4.38 \times 10^{-9}$ |

This study evaluates 5-HT re-uptake inhibition and the $5-HT_{2A}$ and adrenoceptor antagonist activities of KMST in the central nervous and cardiovascular systems. Receptor binding studies have indicated that KMST has a higher affinity for 5-HT re-uptake sites and $5-HT_{2A}$ receptors and has a sharply lower affinity for $\alpha$-adrenoceptors than prazosin. Particularly, it increased blood pressure by microinjection into cisternal and NTS. These facts encouraged us to examine whether KMST offers protection against LPS-induced hypotension and mortality.

Intra-cisternal injection and NTS microinjection of KMST, trazodone and yohimbine increased BP and HR. In fact, injection of the selective $\alpha_2$ antagonist yohimbine into the NTS produced hypertension and tachycardia, possibly because yohimbine antagonizes the postsynaptic effects of endogenously released catecholamines (Kubo et al., 1987). Our results also confirmed that central administration of yohimbine increased BP and HR (Corrêa and Peres-Polon, 1995; Díaz-Cabiale et al., 2000). In our experiment, low dose (0.03 μmol) KMST and yohimbine reduced the centrally effective α2-adrenoceptor agonist clonidine-induced hypotension, but did not inhibit clonidine-induced bradycardia. At a high dose (0.3 μmol), KMST reduced both clonidine-induced hypotension and bradycardia. Since clonidine-like drugs owe part of their bradycardic effect to activation of peripheral cardiac pre-synaptic α2-autoreceptors (Urban et al., 1995), we theorize that KMST and yohimbine at lower doses had no significant effect on peripheral cardiac pre-synaptic α2-autoreceptors. Minimum autonomic activity has been attributed to fluoxetine, and microinjection of this substance into the NTS increased BP and HR (Lane and Baldwin., 1997).

Three subtypes of $\alpha_2$-adrenoceptors, designated as $\alpha_{2A}$, $\alpha_{2B}$ and $\alpha_{2C}$, were proposed by Murphy et al. (1988). The $\alpha_{2A}$-adrenergic subtype is located in the CNS and is concentrated in the cardiovascular control center of the brainstem. $\alpha_{2B}$-adrenergic receptors are located in arterial vascular smooth muscle cells and cause peripheral vasoconstriction (MacMillan et al., 1996; Duka et al., 2000). It is obvious that $\alpha_{2B}$-adrenoceptor agonist activity of clonidine in thoracic aorta produces contractile activity (Fujimoto and Itoh., 1995). In our study, KMST inhibited clonidine-induced vascular contraction; its estimated $pA_2$ value was lower than that of prazosin on $\alpha_2$-adrenoceptors (Table 1). We propose that KMST-mediated inhibition of clonidine-induced contraction is caused by antagonist activity on $\alpha_2$-adrenergic receptors.

Several pharmacologic studies have indicated that $5-HT_{2A}$ receptors mediate the contractile response of blood vessels (Le Roux and Syce, 1989). It has been suggested that both $5-HT_{2A}$ and $5-HT_{1B}$ receptors are involved in vascular contraction (Smith et al., 1999). Our receptor binding experiments showed that KMST had a binding affinity for $5-HT_{2A}$ receptors, but less for $5-HT_{1B}$ receptors (Table 2).

Aryloxypropanolamines are generally recognized as β-adrenoceptor blockers. In pentobarbital-anesthetized rats, intravenous administration of KMST produced a dose-dependent decrease in mean BP and HR and also inhibited phenylephrine- and isoprenaline-induced changes in BP and HR. The estimated $pA_2$ value (6.66) for KMST on $\beta_1$-adrenoceptors of rat left atria was less than that for other β-adrenoceptor blockers (Table 1).

Stimulation by increased plasma catecholamines during early sepsis may cause sympathetic activation of the CVS (Lavicky and Dunn., 1995; Molina-Holgado and Guaza., 1996). This β-adrenergic receptor stimulation may also exercise a beneficial agonist effect on macrophages to increase cAMP and to decrease inflammatory cytokines (Szelényi et al., 2000). The non-selective β-adrenoceptor blocker propranolol prevents the effects of α-adrenoceptor blockade on TNF-α plasma levels induced by LPS and associated cytokine formation in mice (Haskó et al., 1995; Elenkov et al., 1995). β-adrenoceptors may be down-regulated and unable to respond fully to catecholamine-derived β-adrenoceptor agonist and drug-derived β-adrenergic antagonist activities during sepsis. In contrast to previous studies of pindolol (Ko et al., 2002), KMST displayed pindolol-like serotonergic and β-adrenoceptor blocking properties that might contribute to its protective effects against LPS-induced hypotension.

A reciprocally permissive interaction occurs between TNF-α and α-adrenoceptor activation. Changes in pre-synaptic adrenergic sensitivity, as well as in neuronal sensitivity to TNF-α have been implicated in the action of anti-depressant drugs (Nickola et al., 2001). Previous studies have demonstrated a neuro-immune link that enables stress-associated noradrenaline to regulate macrophage-derived TNF via a-adrenergic receptor interactions. Both noradrenaline and $\alpha_2$-adrenergic agonists have been shown to augment LPS-induced TNF production. This augmentation was prevented by the $\alpha_2$-adrenergic antagonist yohimbine (Borysenko, 1984; Glaser et al., 1986; Spengler et al., 1990).

Intravenous LPS in this study produced a biphasic reduction in BP in anesthetized rats (Lin et al., 1999). Both aortic hyporeactivity and the second prolonged hypotensive reaction induced by LPS were inhibited by pretreatments with KMST, yohimbine and trazodone. These facts indicate that $\alpha_2$-adrenoceptor blockade plays an important role in normalizing LPS-induced hypotension (Szelényi et al., 2000). However, the $pD_2$ value of yohimbine at 5 hours was less than that of others and indicated that selective $\alpha_2$-adrenoceptor blockade could not fully inhibit LPS-induced vascular hyporeactivity (Table 4).

Reactive oxygen species, superoxides in particular, have been implicated in the potentiation of iNOS induction in cells (Wu et al., 2002). iNOS inhibitors and antioxidants reduce LPS-induced vascular hyporesponsiveness (Girard et al., 1995; Ülker et al., 2001). Likewise, the anti-oxidant activity of KMST, absent in trazodone and yohimbine, may provide more protection against LPS-induced aortic hyporeactivity and hypotension. NO in the CNS is increased by both the $\alpha_2$-adrenoceptor agonist clonidine and LPS administration. The action of clonidine is dependent on activation of eNOS. The action of LPS is dependent on activation of iNOS (Tseng et al., 1996; Dobrucki et al., 2001). We thus suggest that both clonidine- and LPS-induced hypotension are partly attributed to NO release, which are inhibited by the effects of aminoguanidine on iNOS and by the antagonist activities of KMST on $\alpha_2$-adrenoceptors.

Antioxidants can ameliorate depression of vascular reactivity caused by LPS (Loegering et al., 1995). Among them, ascorbic acid affected macrophage activity in mice during endotoxic shock (Victor et al., 2000). In this regard, the toxic effects of oxygen radicals produced by immune cells can be controlled to certain degree by endogenous anti-oxidants (Victor et al., 2000). We suggest that the anti-oxidant activity of KMST exerts a beneficial effect on immune cells (Table 3). LPS-induced elevations of IL-1$\beta$, IL-6, IFN-$\gamma$ and TNF-$\alpha$ levels were inhibited by KMST (1 mg kg$^{-1}$, i.v.). Trazodone and yohimbine in the same doses reduced only IL-1$\beta$ and TNF-$\alpha$. This difference might be due to KMST's anti-oxidant activity, which more potently reduces LPS-induced cytokine production. In this regard, the relationship between the anti-oxidant effect of KMST and its anti-hypotensive/hyporeactivity effects might relate to the inhibition on cytokine-induced iNOS production (Wu et al., 2002).

The generation of free radicals in biological systems contributes to oxidative stress, including inflammation (Girard et al., 1995). KMST possesses free radical scavenging and anti-peroxidation properties that yohimbine and trazodone lack. This may also account for the fact that KMST more potently reduces LPS-induced hypotension and vascular hyporeactivity than yohimbine and trazodone.

Endotoxicosis causes many metabolic alterations. Hyperglycemia in the early phase of sepsis is caused by a decrease in peripheral tissue glucose uptake relative to the rate of glucose production. In contrast, hypoglycemia in severe septic conditions occurs because the rate of glucose use exceeds the rate of production (Maitra et al., 2000). In the present study, LPS-induced early hyperglycemia at 1 and 3 hours was inhibited by KMST, aminoguanidine and ascorbic acid. However, they did not affect the hypoglycemia at 5 hours. Atenolol, a selective $\beta_1$-adrenergic blocker, does not alter the glucose metabolic response to infection. Under septic conditions, non-selective $\beta$-adrenoceptor blocker propranolol prevents an increase in glucose production (Lang, 1992). Since KMST is a selective $\beta_1$-adrenoceptor blocker, but not a $\beta_2$-adrenoceptor blocker, we suggest that it, like aminoguanidine, inhibits LPS-induced hyperglycemia by decreasing glycogenolysis and gluconeogenesis (Sugita et al., 2002).

Many pathobiochemical alterations occur in endotoxic shock: a dramatic increase in eicosanoid and platelet activation factor production, cytokine release (in particular IL and TNF-$\alpha$, activation of the L-arginine-nitric oxide (NO) pathway, formation of oxygen-centered free radicals and activation of the plasmatic coagulation cascade, fibrinolysis and complement pathway (Szabó and Thiemermann, 1994). In this study, KMST reduced LPS-induced hypotension-associated cytokine formation. Although cytokine levels were not completely inhibited by KMST during the later stage of LPS-induced hypotension, KMST was beneficial in treating the early stage of LPS-induced hypotension. This suggests that other events are involved in the pathogenesis of LPS-induced mortality. In this study, even though KMST did not prevent LPS-induced death, it did prolong survival time. The prolongation of survival and prevention of early hypotension might provide some clinical benefits in improving overall survival of patients in septic shock.

In conclusion, KMST has adrenergic and serotonergic antagonist activities, including possible pindolol-like characteristics. It can reduce and potentially normalize LPS-induced hypotension, as well as generate a CNS-mediated increase in BP. KMST has an antioxidant effect that may contribute to its ability to reduce LPS-induced hypotension and other endotoxic inflammatory responses. Further evaluation of KMST's anti-depressant-related behavior activities is still needed. It is notable that $\alpha_2$-Adrenoceptor blocking properties of KMST and other phenylpiperazine type antidepressants may be beneficial in the treatment of septic shock. KMST's effects, including its $\beta_1$ adrenoceptor blocking activity, on bacteria-induced hypotension requires further investigation.

EXAMPLE 1

1-(3-chlorphenyl-1-piperazinyl)-2-propanol-3-oxy-(2-methoxy-4-propenyl)-benzene or 1-((2-methoxy-4-propenyl)-phenoxy)-3-((3-chlorphenyl-piperazinyl)-2-propanol (1).

3-chlorophenyl piperazine (5 g) was dissolved in methanol (20 ml), mixed with 4-oxy-methyloxirane-3-methoxy-1-propylenyl benzene (20 g), and boiled to reflux at 80° C. for 4 hours. Obtained mixture was then removed the included methanol by reduced pressure using vacuum pump. The residue was passed through silica gel colum chromatography, eluated with n-hexane and ethyl acetate (9:1), dried by reduced pressure, and crystallized with methanol to obtain 13.8 g white crystal of compound 2. 1-((2-methoxy-4-propenyl)-phenoxy)-3-((3-chlorphenyl-piperazinyl)-2-propanol (1).

$^1$H NMR (CDCl$_3$)$\delta$0.07 (CH$_3$), 1.85–1.89 (d, 3H, Ar—CH=CH—CH$_3$), 2.65–2.69 (m, 2H, Ar—O—CH$_2$CH (OH)—CH$_2$—N), 2.72–2.86 (t, 4H, 2×Ar—N—CH$_2$CH$_2$—N—), 3.21–3.26 (t, 4H, 2×Ar—N—CH$_2$CH$_2$—N—), 3.70–3.87 (d, 3H, Ar—O—CH$_3$), 4.02–4.04 (m, 2H, Ar—O—CH$_2$CH—(OH)—CH$_2$—N), 4.13–4.24 (m, 2H, ArOCH$_2$CH—(OH)—CH$_2$—N), 6.13–6.16 (m, 1H, ArCH=CH—CH3), 6.30 (d, 1H, ArCH=CHCH3), 6.75–6.89 (m, 7H, Ar), 7.13–7.26 (m, 6H, Ar—Cl); IR (KBr) 3434, 2932, 2828 cm$^{-1}$; MS m/z 417 (M+H)$^+$.

EXAMPLE 2

1-((4-chlorphenyl-1-1piperazinyl)-2-propanol-3-oxy)-(2-methoxy-4-propenyl)-benzene or 1-((2-methoxy-4-propenyl)-phenoxy)-3-((4-chlorphenyl-piperazinyl)-2-propanol (2).

4-chlorophenyl piperazine (5 g) was dissolved in methanol (20 ml), mixed with 4-oxy-methyloxirane-3-methoxy-1-propylenyl benzene (20 g), and boiled to reflux at 80° C. for 4 hours. Obtained mixture was then removed the included methanol by reduced pressure using vacuum pump. The residue was passed through silica gel colum chromatography, eluated with n-hexane and ethyl acetate (9:1), dried by reduced pressure, and crystallized with methanol to obtain 16.3 g white crystal of compound 2.

$^1$H NMR (CDCl$_3$)$\delta$0.07 (CH$_3$), 1.85–1.89 (d, 3H, Ar—CH=CH—CH$_3$), 2.65–2.71 (m, 2H, Ar—O—CH$_2$CH (OH)—CH$_2$—N), 2.76–2.87 (t, 4H, 2×Ar—N—CH$_2$CH$_2$—N—), 3.16–3.21 (t, 4H, 2×Ar—N—CH$_2$CH$_2$—N—), 3.87

(d, 3H, Ar—O—CH$_3$), 4.02–4.05 (m, 2H, Ar—O—CH$_2$CH—(OH)—CH$_2$—N), 4.12–4.21 (m, 2H, ArOCH$_2$CH—(OH)—CH$_2$—N), 6.06–6.20 (m, 1H, ArCH=CH—CH3),6.30–6.39(d, 1H, ArCH=CHCH3), 6.80–6.90 (m, 7H, Ar), 7.17–7.26 (m, 6H, Ar—Cl); IR (KBr) 3431, 2932, 2826 cm$^{-1}$; MS m/z 417 (M+H)$^+$.

EXAMPLE 3

1-(3-chlorphenyl-1-piperazinyl)-propyloxy-2-methoxy-4-propenyl-benzene or 1-((2-methoxy-4-propenyl)-phenoxy)-3-((3-chlorphenyl-piperazinyl)-propane (3).

1-(3-chlorophenyl)-4-(3-chloropropyl) piperazine HCl (5 g) was dissolved in metnanol (20 ml), mixed with isoeugenol (20 g) to reflux at 80° C. for 4 hours. Obtained mixture was then removed the included methanol by reduced pressure using vacuum pump. The residue was passed through silica gel colum chromatography, eluated with n-hexane and ethyl acetate (9:1), dried by reduced pressure, and crystallized with methanol to obtain 17.4 g white crystal of compound 3.

$^1$H NMR (CDCl$^3$)δ0.07 (CH$_3$), 1.85–1.89 (d, 3H, Ar—CH=CH—CH$_3$), 1.98–2.12(m, 2H, Ar—O—CH$_2$CH$_2$—CH$_2$—N), 2.59–2.64 (t, 4H, 2×Ar—N—CH$_2$CH$_2$—N—), 3.18–3.23 (t,4H, 2×Ar—N—CH$_2$CH$_2$—N—), 3.87 (d, 3H, Ar—O—CH$_3$),4.06–4.09 (m, 2H, Ar—O—CH$_2$CH$_2$—CH$_2$—N), 4.12–4.13 (m, 2H,ArOCH$_2$—CH$_2$—CH$_2$—N), 6.01–6.19 (m, 1H, ArCH=CH—CH3), 6.30–6.40 (d, 1H, ArCH=CHCH3), 6.76–6.90 (m, 7H, Ar), 7.12–7.26 (m, 6H, Ar—Cl); IR (KBr) 2951, 2618 cm$^{-1}$; MS m/z 401 (M+H)$^+$.

The compound of this invention will include various excipients; carriers or diluents and pharmaceutically approved pH of processed salts in accordance to necessity to form composition with therapeutic efficacy. Such pharmaceutical preparation could be in solid form for oral and rectum administration; liquid form or non-intestinal injection form; or ointment form for direct application on affected part. Such solid forms are manufactured according to common pharmaceutical preparation methods, which will include disintegrant like starch; sodium carboxymethylcellulose, adhesive like ethanol; glycerine, or magnesium stearic acid; lactose to make into pharmaceutical preparation like tablets or filled into capsules or suppository. Solution or saline that include this novel compound as ingredient could use buffers of phosphoric nature to adjust the pH to suitable level, before adding adjutant; emulsifier to produce injection dose or other liquid preparation. This novel compound or pharmaceutical manufacturing can be mixed with synthetic acid salts and various fundamental preparations to form ointments according to known pharmaceutical manufacturing methods. Pharmaceutical compounds having this invention compound as a major ingredient could be used on mammals to produce the efficacy of this main ingredient. General dosage could be adjusted according to the degree of symptoms, and normally a person will require a dosage of 50 to 300 mg each time, three times per day.

What is claimed is:
1. A compound, having the formula I:

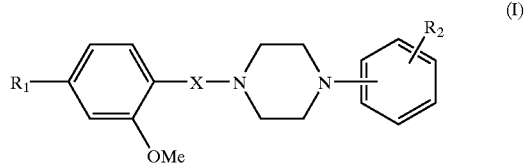

(I)

where R$_1$ is selected from the group consisting of an alkyl group and an alkenyl group;
X represents

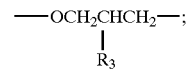

—OCH$_2$CHCH$_2$—;
|
R$_3$

R$_2$ is selected from the group consisting of a halogen group, —NH$_2$, —NO$_2$ and a hydrogen group;
R$_3$ is selected from the group consisting of a hydrogen group and a hydroxyl group.

2. The compound of claim 1, wherein said halogen group is selected from the group consisting of F, Cl, Br, and I.

3. A method of manufacturing a compound having the formula I, said method comprising the steps of:
preparing 4-oxy-methyloxirane-3-methoxy-1-propylenyl benzene or its derivative;
mixing phenyl piperazine dissolved in methanol with said 4-oxy-methyloxirane-3-methoxy-1-propylenyl benzene or said its derivative to reflux at 100° C. for approximately 2 to approximately 6 hours;
removing the methanol from the mixture;
passing the mixture through a silica gel column chromatography after the removing step;
eluting the passed mixture with n-hexane and ethyl acetate;
drying the eluted mixture; and
crystallizing the dried mixture with methanol to obtain the compound having the formula I:

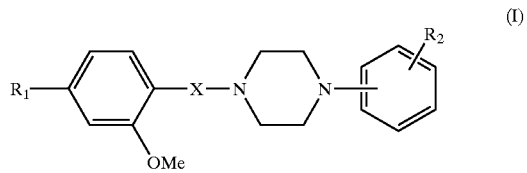

(I)

where R$_1$ is selected from the group consisting of an alkyl group and an alkenyl group;
X represents

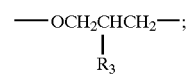

—OCH$_2$CHCH$_2$—;
|
R$_3$

R$_2$ is selected from the group consisting of a halogen group, —NH$_2$, —NO$_2$ and a hydrogen group;
R$_3$ is selected from the group consisting of a hydrogen group and a hydroxyl group.

4. The method of claim 3, wherein said 4-epoxy isoeugenol is prepared by a process comprising the steps of:

mixing epichlorohydrin with isoeugenol and NaOH dissolved in ethanol;

boiling the mixture to reflux for 2–6 hours;

removing the ethanol from the mixture after the boiling step;

passing the mixture through a silica gel column chromatography;

eluting the mixture with n-hexane and ethyl acetate after the passing step; and drying the eluted mixture with reduced pressure to obtain 4-oxy-methyloxirane-3-methoxy-1-propylenyl benzene.

5. A pharmaceutical composition, comprising a compound having the formula I:

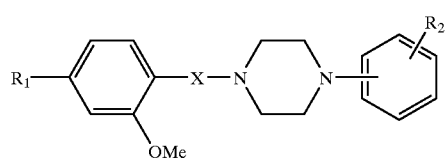

where $R_1$ is selected from the group consisting of an alkyl group and an alkenyl group;

X represents

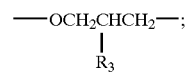

$R_2$ is selected from the group consisting of a halogen group, —$NH_2$, —$NO_2$ and a hydrogen group;

$R_3$ is selected from the group consisting of a hydrogen group and a hydroxyl group.

6. The pharmaceutical composition of claim 5, wherein said halogen group is selected from the group consisting of F, Cl, Br, and I.

7. The pharmaceutical composition of claim 6, wherein said pharmaceutical composition has $\alpha_2$-adrenergic/5-$HT_{2A}$ antagonist activity.

8. The pharmaceutical composition of claim 6, wherein said pharmaceutical composition has 5-HT re-uptake activity.

9. The pharmaceutical composition of claim 6, wherein said pharmaceutical composition has anti-oxidant activity.

10. The pharmaceutical composition of claim 6, wherein said pharmaceutical composition has $\alpha_2$-adrenergic/5-$HT_{2A}$ antagonist activity, 5-HT re-uptake activity, and anti-oxidant activity.

* * * * *

UNITED STATES PATENT AND TRADEMARK OFFICE
CERTIFICATE OF CORRECTION

PATENT NO. : 6,887,878 B2
DATED : May 3, 2005
INVENTOR(S) : Ing-Jun Chen

It is certified that error appears in the above-identified patent and that said Letters Patent is hereby corrected as shown below:

Title page,
Item [73], Assignee, correct "Syn-Rech Chem & Phan Co., Ltd," to
-- Syn-Tech Chem. & Pharm. Co., Ltd. --.

Signed and Sealed this

Sixteenth Day of August, 2005

JON W. DUDAS
*Director of the United States Patent and Trademark Office*